(12) United States Patent
Solazzi

(10) Patent No.: US 7,981,380 B2
(45) Date of Patent: Jul. 19, 2011

(54) SAMPLE CUP WITH THIN-FILM DETACHMENT MECHANISM

(76) Inventor: Monte J. Solazzi, Palm City, FL (US)

( * ) Notice: Subject to any disclaimer, the term of this patent is extended or adjusted under 35 U.S.C. 154(b) by 359 days.

(21) Appl. No.: 11/705,566

(22) Filed: Feb. 12, 2007

(65) Prior Publication Data

US 2007/0189933 A1     Aug. 16, 2007

Related U.S. Application Data

(60) Provisional application No. 60/772,505, filed on Feb. 10, 2006.

(51) Int. Cl.
*G01N 21/75* (2006.01)
(52) U.S. Cl. ...... 422/400; 600/562; 422/549; 73/864.91
(58) Field of Classification Search .......... 422/102, 422/104; 378/44; 73/864.91
See application file for complete search history.

(56) References Cited

U.S. PATENT DOCUMENTS

| 3,010,598 | A | * | 11/1961 | Foss | 220/4.26 |
| 5,020,690 | A | * | 6/1991 | Kishikawa et al. | 222/83 |
| 5,146,828 | A | * | 9/1992 | Huang et al. | 83/570 |
| 5,630,989 | A | | 5/1997 | Solazzi | |
| 6,009,766 | A | * | 1/2000 | Solazzi | 73/864.91 |
| 6,428,751 | B1 | * | 8/2002 | Solazzi | 422/102 |
| 2007/0116613 | A1 | * | 5/2007 | Elsener | 422/102 |

\* cited by examiner

*Primary Examiner* — Max Hindenburg
*Assistant Examiner* — Renee Danega
(74) *Attorney, Agent, or Firm* — Plevy & Keene LLP

(57) ABSTRACT

A cup assembly for holding a sample to be analyzed spectrochemically, including a sample cell having a generally cylindrical wall longitudinally extending between a first end and a second end thereof and a sleeve having a generally cylindrical wall longitudinally extending between a first end and a second end thereof, and a plurality of projections longitudinally extending from the first end of the sleeve wall. When a substantially planar film is interposed between the sample cell and the sleeve, and the first end of the sample cell is inserted into the first end of the sleeve, the film is retained between the sample cell and the annular sleeve; and the longitudinal projections are positioned to perforate the film when the film is pulled against the longitudinal projections.

18 Claims, 3 Drawing Sheets

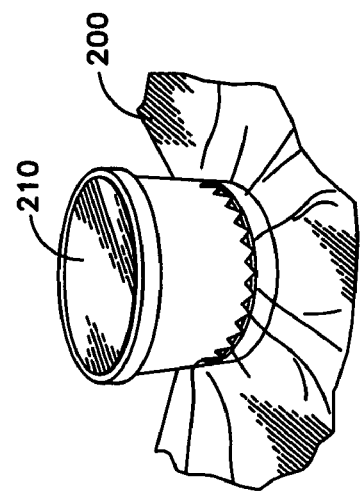
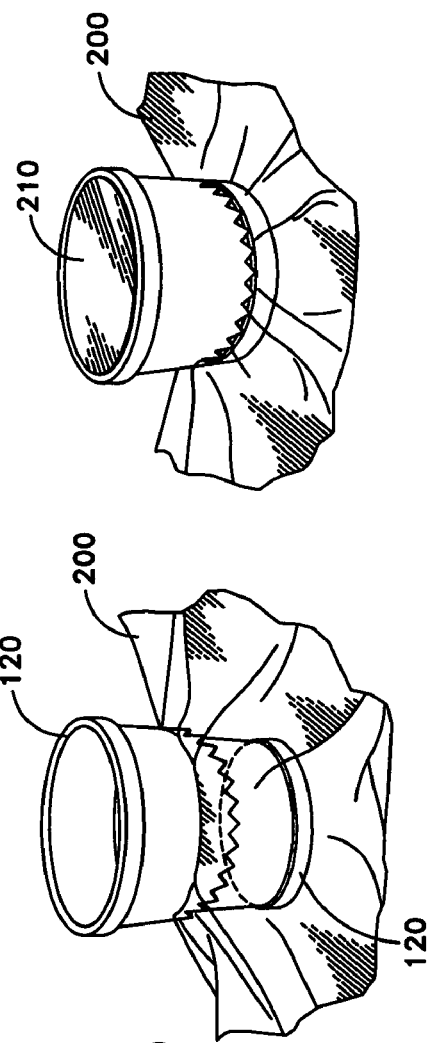
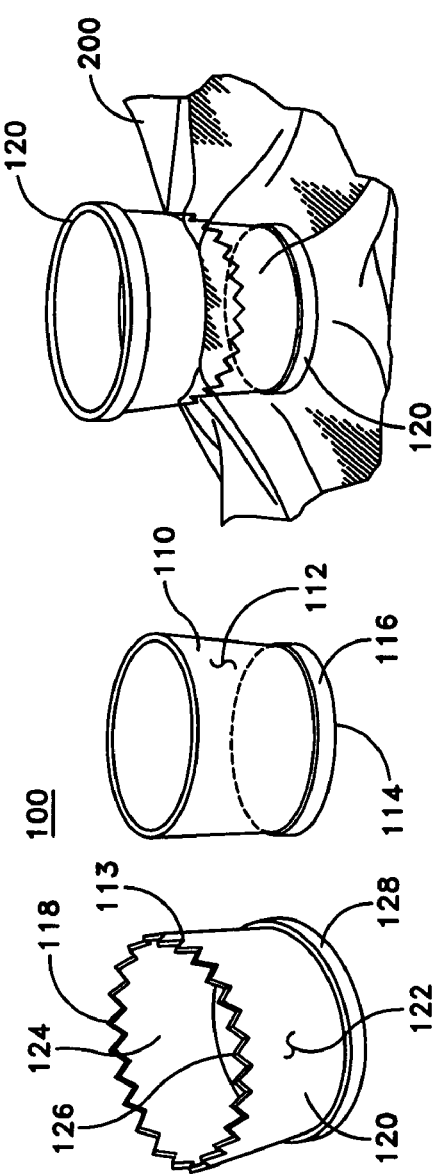
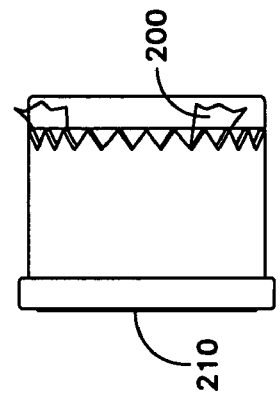
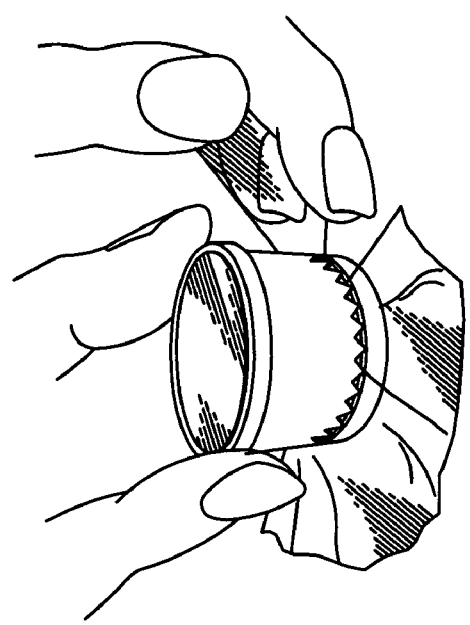
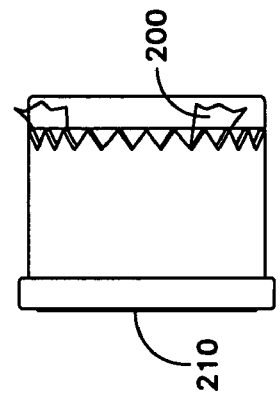
FIG. 1
FIG. 2
FIG. 3
FIG. 4
FIG. 5
FIG. 6

_US 7,981,380 B2_

SAMPLE CUP WITH THIN-FILM DETACHMENT MECHANISM

RELATED APPLICATION

This application claims priority of U.S. patent application Ser. No. 60/772,505, filed Feb. 10, 2006, entitled SAMPLE-CUP WITH THIN-FILM DETACHMENT MECHANISM, the entire disclosure of which is incorporated by reference herein.

FIELD OF THE INVENTION

This invention relates to a sample cup for use in holding specimens for spectrochemical analysis, and more particularly to a sample cup comprised of a collar that pulls a thin-film material taut over the open end of cell body, thereby obstructing one end of the cell body and closing the sample cup.

BACKGROUND OF THE INVENTION

The use and applications of thin-films to close substance containing sample cups are well recognized. An example of such a sample cup is disclosed in U.S. Pat. No. 5,630,989, entitled APPARATUS FOR TRIMLESS SAMPLE CUP USED IN X-RAY SPECTROSCOPY, the entire disclosure of which is hereby incorporated by reference herein.

When a sheet of thin film material is positioned over the open end of a cell body by means of the annular collar or sleeve, one or more portions of the thin film material extend beyond the collar. These excess portion(s) of the thin film may have a tendency to flare away from the sides of the cell body. As such, the excess thin film material must typically be trimmed from the sides of the cell body, in order that the sample cup may be conveniently handled.

Further, to ensure proper accommodation and precise positioning in sample cup holding instrumentation, extraneous thin-film surrounding the assembled sample cup must typically be meticulously trimmed very close to the sample cup cell body. Residual thin-film portions remaining attached to the sample cup may lead to sample cup misalignment in instrumentation. Alignment inaccuracies potentially affect the analytical accuracy of spectroscopy and analysis.

Heretofore, the conventional method of trimming excess thin-film has been with the use of scissors. This is a detailed, time-consuming procedure for an analyst, especially when one considers that thin films are inherently prone to static electrical charge build-up. The thin-film clippings are typically annoyingly troublesome—as they cling to virtually any nearby surface, including the thin-film remaining attached to the sample cup. This potentially alters the transmission effects of radiation though the thin film window, in turn adversely affecting the spectrochemical analysis. In instances that dictate a relatively large number of sample preparations and throughput, applying a scissors to trim the extraneous thin-film is not a practical approach.

In response to this need, a sample cup integrated with a mechanism for detaching thin-film portions near the sample cup cell is desired.

BRIEF DESCRIPTION OF THE DRAWINGS

Understanding of the present invention will be facilitated by considering the following detailed description of the preferred embodiments of the present invention taken in conjunction with the accompanying drawings, in which like numerals refer to like parts, and:

FIG. 1 illustrates a sample cup cell and sleeve incorporating a serrated edge;

FIG. 2 illustrates the sample cup cell and sleeve of FIG. 1 with a film interposed there between;

FIG. 3 illustrates the sample cup cell and sleeve of FIG. 1 with the sleeve advanced over the film and cell;

FIG. 4 illustrates the sample cup cell and sleeve of FIG. 1 with the sleeve advanced over the film and cell and portion(s) of the film being removed;

FIGS. 5 and 6 illustrate the sample cup cell and sleeve of FIG. 1 with the sleeve advanced over the film and cell and portion(s) of the film removed;

DETAILED DESCRIPTION OF THE PREFERRED EMBODIMENTS

It is to be understood that the figures and descriptions have been simplified to illustrate elements that are relevant for a clear understanding of the present invention, while eliminating, for the purpose of clarity, many other elements found in typical sample cups and methods of making and using the same. Those of ordinary skill in the art may recognize that other elements and/or steps are desirable and/or required. However, because such elements and steps are well known in the art, and because they do not facilitate a better understanding of the present invention, a discussion of such elements and steps is not provided herein.

Figure 7:
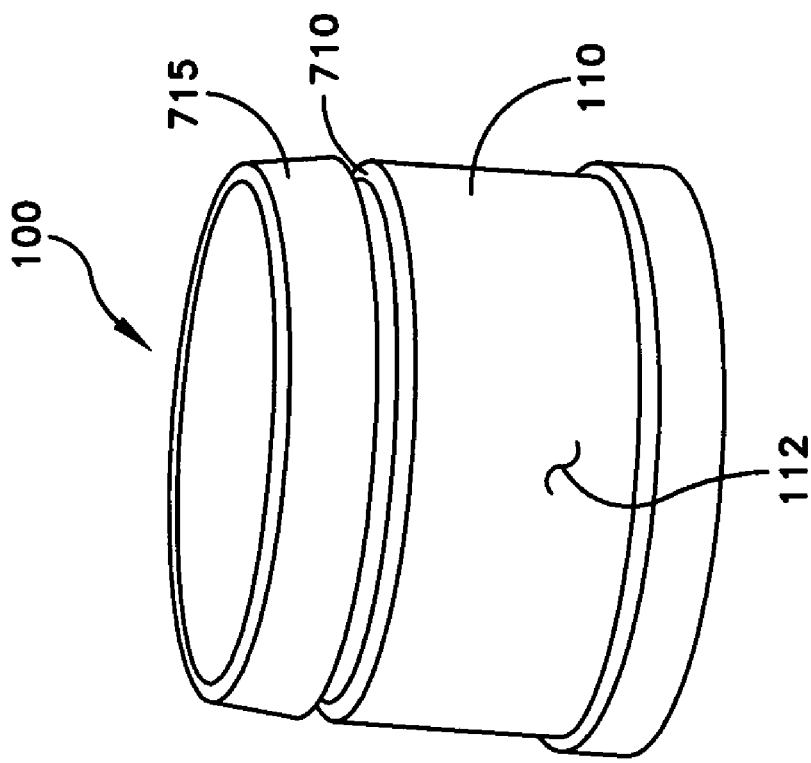
FIG. 7 illustrates a sample cup cell and sleeve incorporating a serrated edge.
Figure 7:
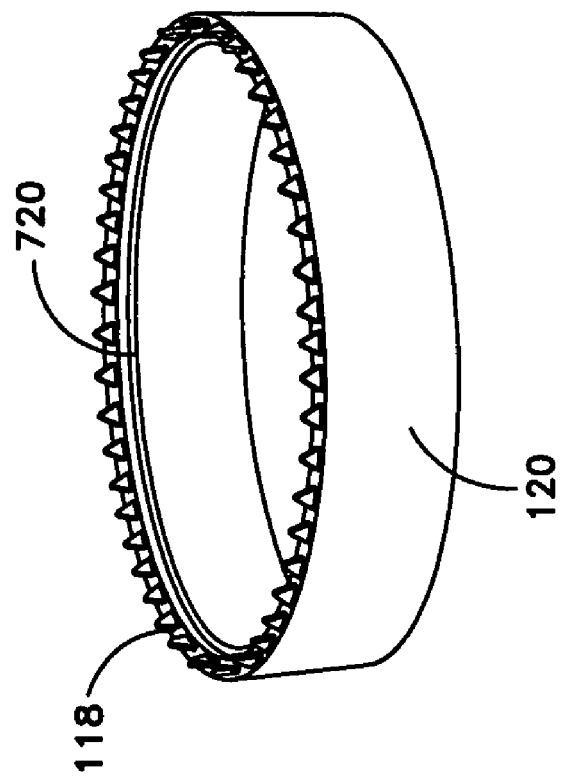

Referring now to FIG. 1, there is shown a sample cup assembly 100. In the illustrated embodiment, sample cup assembly 100 includes a main cell body 110, a substantially planar thin film material 200 (see, FIGS. 2-6) and an annular collar or sleeve 120. Sleeve 120 may take the form of a collar, snap-on ring, sleeve or any other device of similarity, to firmly affix thin-film 200 over the cell 110 opening. The cell 110 window (210, FIG. 5) formed by thin-film 200 represents the point of entry for irradiating a sample substance within the cell 110 for spectrochemical analysis. Cell 110 and sleeve 120 may each be formed of plastic, for example. In one particular embodiment, they are around 1.20-1.23 inches in diameter, have an internal aperture of around 0.95-0.97 inches and are around 0.8-1 inch tall. Of course, other sizes are contemplated. Further, sleeve 120 may optionally be considerably shorter than the cell (as is shown in the embodiment of FIG. 7).

Referring again to FIG. 1, cell 100 includes a side-wall portion 112 extending longitudinally an open end of cell 100 and an end portion 114. A flange 116 is positioned around end portion 114. The side-wall and end portions 112, 114 define an open-ended inner cavity, or hollow. Similarly, sleeve 120 includes a side-wall portion 122 extending longitudinally between open ends 124, 126. A flange 128 is positioned around open end 126. Open-end 124 of sleeve 120 is adapted to receive the open end of the cell 110.

By way of further non-limiting example only, apparatus 100 may optionally exhibit many of the features presented by the afore-incorporated U.S. Pat. No. 5,630,989. For example, cell body 110 may define a sample retaining region and a reservoir region. The sample retaining region of cell body 100 may be tubular in shape having an open end and a closed end defined by side-wall portion 112 and end portion 114. Side-wall 112 may be generally cylindrical and longitudinally extend from the closed end up to the open end. As such, side-wall 112 and end-portion 114 define a hollow capable of retaining a sample specimen (not shown). The outside of side-wall 112 may be tapered toward the open end of the sample retaining region. The edge of the side-wall 112 proximate the open end may be rounded or squared.

If incorporated, a taper of the side-wall 114 ends at the reservoir region 840 (in FIG. 8) defined by flange 116. The reservoir region surrounds and extends below the closed end 114 of the sample retaining region. A venting provision may be disposed within the closed end. The venting provision may be optionally ruptured, thereby allowing the interior hollow of cell body 110 to communicate with the reservoir region. As such, any sample contained within the sample retaining region hollow can be vented to the reservoir region.

Annular collar or sleeve 120 is useful for properly positioning the thin film material across the opening of cell body 110. Sleeve 120 is generally tubular having first and second, oppositely disposed open ends. Side-wall 122 may have an interior surface that is tapered at an angle of inclination supplementary to the angle of inclination of the outside of side-wall 112 of cell body 110. One or more projections and mating recesses may be used to couple cell body 110 to sleeve 120. For example, one or more ring projections and matching ring recesses may circumnavigate side-walls 112, 122.

According to an aspect of the present invention, sleeve 120 incorporates a series of projections 118 on an outermost edge 113 of side-wall 122 proximate open end 124 thereof. Projections 118 may be sharp or blunt, for example. Projections 118 may be adapted to both perforate or puncture thin film 200 (FIGS. 2-6), and secure a remaining portion of thin film 200 (FIGS. 2-6) after perforation, thereby closing the open end of the cell 100 interior hollow. Projections 118 may be regularly (or irregularly) spaced along the edge 113. It is also understood that the projections may be more blade shaped in terms of a knife edge that gradually extends in height about the circumference of the sleeve.

Referring again to FIG. 2, in use thin film 200 is interposed between cell body 110 and the protrusions 118 of sleeve 120. Thin film 200 is positioned over the open end of cell body 100. According to an embodiment of the present invention, thin film material 200 is flexible and transparent to radiant energy used in spectrochemical analysis. The possible compositions of such thin film materials 200 are well known in the art and need not be set forth herein at length. Projections 118 collectively represent foci for perforating thin-film 200 for subsequent detachment from the assembled sample cup. Sleeve 120 is positioned over film 200 and around cell body 110. Sleeve 120 and cell body 110 may mate in a conventional manner using one or more projections and one or more receiving portions, such as conventional tabs and recesses, for example. The cell/film/sleeve assembly may optionally be inverted after mating to aid in thin film trimming.

Referring to FIGS. 3 and 4, by pulling the extraneous portion(s) of thin-film 200 against projections 118, a substantially uniform line of perforations in film 200 is created substantially conforming to the configuration of the securing collar or sleeve 120. In the illustrated embodiment, cell body 110 and sleeve 120 are circular in cross-section, although other configurations can be used. With increasing force, thin-film 200 breaks away in an intact circular pattern defined by the perforations.

Referring now also to FIGS. 5 and 6, thin-film detachment is at the juncture of the upper end of the collar, sleeve or snap-on ring 120 and closely intimate to the assembled sample cup cell 100. This facilitates the unobstructed alignment of the assembled sample cup in instrumentation sample cup holders, thereby averting any ramifications of any residual thin-film remaining attachment.

Referring now also to FIG. 7, there is illustrated another embodiment of the invention. Sampling cup assembly 100 thereof again includes a sample cup cell body 110 and a snap-on ring or sleeve 120. The edge of the snap-on ring or sleeve 120 again incorporates projections 118. In the embodiment of FIG. 7, the length or height of the snap-on ring or sleeve 120 is substantially smaller than the length of the sample cup cell 100. The ring recess mentioned earlier may be in the form of a continuous semicircular groove 710 disposed in the side-wall 112. The semicircular groove may be continuous across the side-wall 112 or it may be segmented. The ring projection mentioned earlier may be a semicircular protrusion 720 disposed on the inner surface of the side-wall 122. The semicircular protrusion 720 may be continuous across the side-wall 122 or it may be segmented. When the cell body 110 is inserted in the end of the sleeve 120, the slight interference fit between the side-wall 122 and the sleeve 120 increases the tautness of a film 200 (in FIGS. 2-6) interposed between the cell body 110 and the sleeve 120. The protrusion(s) 720 lodge(s) into the groove 710 and secures the sleeve 120 to the cell body 110 while maintaining the tautness in the film 200 across the open end of the cell body 110.

In an embodiment of the invention, a portion 715 of the cell body 110 above the groove 710 may be frustoconical in shape converging towards the first end of the sample cell body 110. Correspondingly, the ring or sleeve 120 may also be frustoconically shaped such that it converges from the first end 124 of the sleeve 120 to the second end 126 of the sleeve 120.

Figure 8:
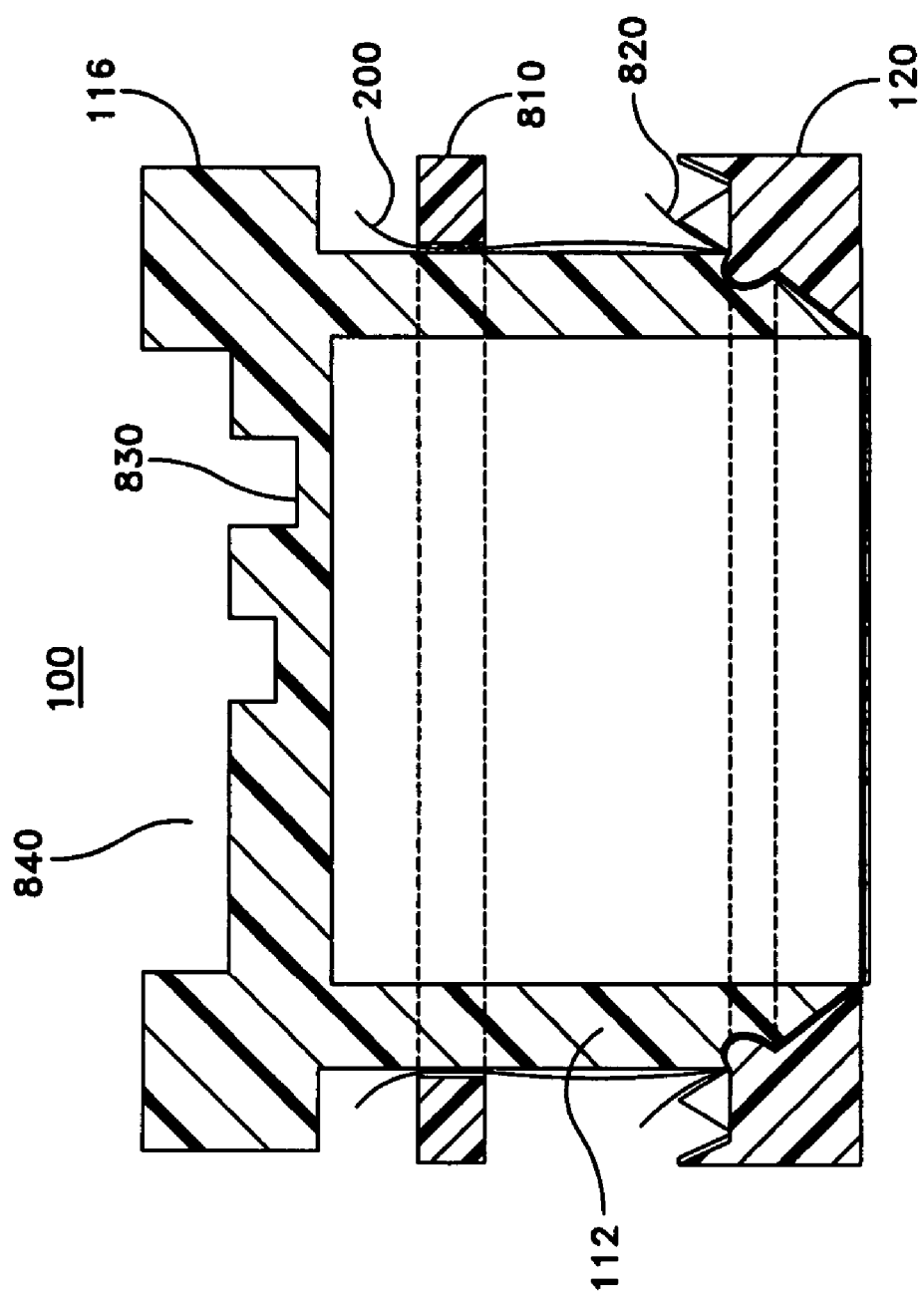
FIG. 8 illustrates a cross-sectional view of an embodiment of a sample cup sell, a collar and a sleeve incorporating a serrated edge.

Now referring to FIG. 8, another embodiment of the invention is illustrated. A collar 810 is further included and used to initially secure a film 200 to the sample cell body 110 along the side-wall 112. A sample is then placed on film 200. The sample may be a powder or liquid droplet for example. Another film 820 is then placed across the open end of the sample cell body 110, over film 200 and the sample such that the sample is sandwiched between the two film layers. The snap-on ring 120 is locked to the sample cell body 110 via ring recess(es) and ring protrusion(s). The collar 810 and the snap-on ring 120 cooperatively hold the films 200, 820 tautly against the open end of the sample cell body 100.

Those of ordinary skill in the art may recognize that many modifications and variations of the present invention may be implemented without departing from the spirit or scope of the invention. Thus, it is intended that the present invention covers the modifications and variations of this invention.

What is claimed is:

1. A cup assembly for holding a sample to be analyzed spectrochemically, comprising:
   a sample cell body having a generally cylindrical wall longitudinally extending between a first end and a second end thereof and an outwardly extending annular flange unitarily formed with said second end of said sample cell body;
   an annular sleeve having a generally cylindrical wall longitudinally extending between a first end and a second end thereof, and a plurality of projections longitudinally extending from the first end of the sleeve; and
   a substantially planar film interposed between the sample cell body and the annular sleeve,
   wherein, upon assembly, the first end of the sample cell body is inserted into the first end of the annular sleeve to retain a portion of the film between the sample cell body and the annular sleeve and said plurality of projections engage said annular flange to create one or more perforations in the film, wherein the portion of the film extending beyond the first end of the sleeve is removed by pulling the film against the plurality of projections.

2. The cup assembly according to claim 1, wherein said substantially planar film is transparent to radiant energy utilized in spectrochemical analysis.

3. The cup assembly according to claim 1, wherein said plurality of projections is regularly spaced along said first end of the sleeve wall.

4. The cup assembly according to claim 1, wherein at least one of said plurality of projections is sharp.

5. The cup assembly according to claim 1, wherein at least one of said plurality of projections is blunt.

6. The cup assembly according to claim 1, further comprising:
a recess extending circumferentially, at least partially, about an outer surface of said wall of said sample cell body; and
a protrusion extending circumferentially, at least partially, about an inner surface of said wall of said sleeve, said protrusion adapted and constructed so as to fit within said recess;
wherein when the first end of said sample cell body is inserted into the first end of the sleeve, said protrusion lodges into said recess and secures said sleeve to the sample cell body.

7. The cup assembly according to claim 1, wherein the projections are blade shaped and gradually extending in height about the circumference of the sleeve.

8. The cup assembly according to claim 1, wherein said sample cell body is provided with an end wall at said second end, said end wall defining a centrally disposed reduced thickness region which is rupturable to permit atmospheric venting of said sealed cup.

9. The cup assembly according to claim 1, wherein said sleeve has a length substantially smaller than the length of said wall of said sample cell body.

10. The cup assembly according to claim 1 further comprising a substantially cylindrical wall extending from said annular flange, said substantially cylindrical wall extending in a direction opposite to that of said first end, said wall and said cylindrical wall defining a reservoir for containing heat sensitive liquid samples.

11. A cup assembly for holding a sample to be analyzed spectrochemically, comprising:
a sample cell body having a generally cylindrical wall which extends between a first end and a second end thereof and an outwardly extending annular flange unitarily formed with said second end of said sample cell body;
a sleeve having a generally cylindrical wall having a first end and a second end;
a substantially planar thin film;
a first means for perforating said substantially planar thin film, said first means integrally formed in said sleeve wall and longitudinally extending from said first end of said sleeve; and
a second means for retaining the substantially planar thin film placed across the first end of said sample cell body and for securing said sleeve to said sample cell body, said second means associated with each of said walls of said sample cell body and sleeve;
wherein, upon assembly, said sample cell body and sleeve retain a portion of the thin film placed across said first end of said sample cell body, said second means pulls an overhanging portion of the thin film down around the entire outer surface of said wall of said sample cell body thereby progressively increasing the tautness of the thin film extending across the first end of the sample cell body and secures said sleeve to said sample cell body, and said first means allows the thin film to be perforated when engaged with said second means and the portion of the thin film extending beyond said first end of said sleeve to be removed from the cup assembly.

12. The cup assembly according to claim 11, wherein
said second means comprises a recess extending circumferentially about an outer surface of said wall of said sample cell body and a circumferentially extending bead projecting from an inner surface of said wall of said sleeve; and
said first means comprises a plurality of projections extending longitudinally from said first end of said sleeve, adapted to perforate the thin film.

13. The cup assembly according to claim 11, wherein said second means comprises a frustoconically shaped outer surface defined by said wall of said sample cell body that converges continuously from said second end to said first end and a frustoconically shaped inner surface which converges continuously from said first end to said second end of said second member.

14. The cup assembly according to claim 11, wherein said second end of said sample cell body is provided with an end wall defining a centrally disposed reduced thickness region which is rupturable to permit atmospheric venting of said sample cup.

15. The cup assembly according to claim 11, said sample cell body further comprises an outwardly extending annular flange unitarily formed with said second end of said sample cell body.

16. The cup assembly according to claim 15, further comprising a substantially cylindrical wall extending from said annual flange in a direction opposite to that of said first end, said end wall and said substantially cylindrical wall defining a reservoir for containing heat sensitive liquid samples.

17. The cup assembly according to claim 11, wherein said sleeve has a length substantially smaller than the length of said wall of said sample cell body.

18. A cup assembly for holding a sample to be analyzed spectrochemically, comprising:
a sample cell body having a generally cylindrical wall longitudinally extending between a first end and a second end thereof;
a sleeve having a generally cylindrical wall longitudinally extending between a first end and a second end thereof, and a plurality of projections longitudinally extending from the first end of the sleeve wall;
a collar having a generally cylindrical wall longitudinally extending between a first end and a second end thereof; and
first and second substantially planar films;
wherein, when the first substantially planar film is interposed between the sample cell body and the collar, and the first end of the sample cell body is inserted into the first end of the collar, the first film is retained between the sample cell body and the collar, and when the collar is moved along the wall of said sample cell body towards the second end, the tautness of the first film across the first end increases, and when the second substantially planar film is placed over said first substantially planar film and the first end of the sample cell is inserted into the first end of the sleeve, a portion of the second film is retained between the cell body and the sleeve and said projections are positioned to perforate the second film one or more locations when engaged with said collar, said one or more perforations allowing said second film to separate at said one or more locations when the portion of the second film extending beyond the sleeve is pulled against the plurality of projections.

* * * * *